United States Patent
Bracht

(10) Patent No.: US 7,332,180 B2
(45) Date of Patent: Feb. 19, 2008

(54) TRANSDERMAL THERAPEUTIC SYSTEM FOR ADMINISTERING NON-STEROIDAL ANTIPHLOGISTIC AGENTS CONTAINING CARBOXYL GROUPS, AND A METHOD FOR THE PRODUCTION OF THE SAME

(75) Inventor: Stefan Bracht, Ochtendung (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 621 days.

(21) Appl. No.: 10/470,701

(22) PCT Filed: Jan. 17, 2002

(86) PCT No.: PCT/EP02/00417

§ 371 (c)(1),
(2), (4) Date: Sep. 22, 2003

(87) PCT Pub. No.: WO02/060418

PCT Pub. Date: Aug. 8, 2002

(65) Prior Publication Data

US 2004/0071764 A1 Apr. 15, 2004

(30) Foreign Application Priority Data

Jan. 30, 2001 (DE) .............................. 101 03 860

(51) Int. Cl.
*A61K 9/70* (2006.01)
*A61K 9/14* (2006.01)
*A61K 31/56* (2006.01)
*A61F 13/00* (2006.01)
*A01N 45/00* (2006.01)

(52) U.S. Cl. ........................ 424/449; 424/484; 514/169

(58) Field of Classification Search ................ 424/449, 424/484; 514/169
See application file for complete search history.

(56) References Cited

U.S. PATENT DOCUMENTS 5,125,995 A 6/1992 D'Haese et al.

(Continued)

FOREIGN PATENT DOCUMENTS

DE 40 20 144 C2 1/1992

(Continued)

OTHER PUBLICATIONS

Goodman and Gilman, The Pharmacological Basis of Therapeutics, 1990, Pergamon Press, 8th edition, pp. 638 & 664.*

(Continued)

*Primary Examiner*—Johann R. Richter
*Assistant Examiner*—Konata M. George
(74) *Attorney, Agent, or Firm*—Birch, Stewart, Kolasch & Birch, LLP

(57) ABSTRACT

A transdermal therapeutic system (TTS) with a content of at least one active substance from the group of the carboxyl group-containing non-steroidal antirheumatics, which has a backing layer (1), an active substance-containing matrix layer (2) and a detachable protective layer (3), is characterized by a matrix layer (2) based on a carboxyl group-containing polyacrylate pressure-sensitive adhesive, which matrix layer (2) has a content of oleic acid and potassium ions, with the constituent amount of the potassium ions being in the range of from 5 to 50%, relative to the equivalent weight of the sum of all carboxyl group-containing matrix components.

18 Claims, 1 Drawing Sheet

Figure 1:
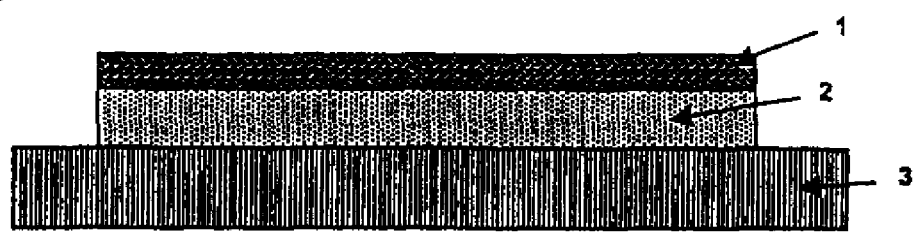

U.S. PATENT DOCUMENTS 5,906,830 A * 5/1999 Farinas et al. .............. 424/448

FOREIGN PATENT DOCUMENTS

| | | |
|---|---|---|
| DE | 197 06 824 C1 | 3/1998 |
| DE | 198 30 649 A | 1/2000 |
| DE | 198 30 649 A1 | 1/2000 |
| DE | 199 18 106 A | 10/2000 |
| DE | 199 18 106 A1 | 10/2000 |
| EP | 0 446 636 A | 9/1991 |
| EP | 0 965 626 A | 12/1999 |
| JP | 4-74119 A | 3/1992 |

OTHER PUBLICATIONS

Patent Abstract of Japan. vol. 016, No. 283 (C-0955), Jun. 24, 1992 & JP 04 074119 A, Mar. 9, 1992.

* cited by examiner

TRANSDERMAL THERAPEUTIC SYSTEM FOR ADMINISTERING NON-STEROIDAL ANTIPHLOGISTIC AGENTS CONTAINING CARBOXYL GROUPS, AND A METHOD FOR THE PRODUCTION OF THE SAME

This application is the national phase under 35 U.S.C. § 371 of PCT International Application No. PCT/EP02/00417 which has an International filing date of Jan. 17, 2002, which designated the United States of America.

The present invention relates to transdermal therapeutic systems (TTS) intended for the administration of carboxyl group-containing, non-steroidal antiphlogistics. The invention more specifically relates to TTS of the above-mentioned kind which have a matrix based on carboxyl group-containing polyacrylate pressure-sensitive adhesives. The present invention further comprises processes of producing the TTS of the above-mentioned kind.

Active substances of the group of carboxyl group-containing non-steroidal antirheumatics or antiphlogistics (NSAID) are widely used in the treatment of inflammations, inflammatory arthropacies, rheumatic syndromes, and of the conditions of pain caused thereby.

Substances belonging to this group of active substances are, on the one hand, members of the group of derivatives of acetic acid, such as, for example, indomethacin, acemetacin, tolmetin, diclofenac and lonazolac, and on the other hand, members of the group of propionic acid derivatives (profens), such as, for example, ibuprofen, flurbiprofen, fenoprofen, ketoprofen, naproxen and tiaprofen. Since oral intake frequently causes side effects such as gastric disorders and haemorrhages in the gastrointestinal region, the topical or transdermal administration is in principle preferable. This can be done using gels, creams, ointments or patches sticking to the skin. The latter have the additional advantage that they can remain at the application site for a prolonged period—unlike, for example ointments—and that their application is easier.

TTS which have a content of NSAID are known for example from DE 198 30 649 A1. This publication, as well as the statements made therein concerning the state of the art is expressly included herein by way of reference.

From DE 198 30 649 A1 it emerges that with a combination of NSAID, especially ketoprofen, flurbiprofen or ibuprofen, with fatty acids as permeation enhancers and a carboxyl group-containing adhesive matrix it is possible to achieve high release rates.

However, further studies have now resulted in the finding that the matrix formulations according to the example 1, 2 and, in particular, 3 in DE 198 30 649 A1 have a very soft consistency and highly dissatisfactory cohesive properties, due to their high content of active substance and plasticizing fatty acids. In addition, in the freshly prepared state, problems were observed, both when PET films and elastic PET fabrics were used, with respect to anchorage of the active substance-containing matrix layer, in particular on polyethylene terephthalate (PET), which is used as backing layer. This is a disadvantage especially because of the fact that PET is the most highly preferred material for backing layers since it has a barrier property to active substances as well as because of its ability to endure mechanical stress. As a consequence, poor anchorage of the active substance matrix on such PET materials entails great limitations in the use of the formulations disclosed in DE 198 30 649 A1 for producing TTS which contain carboxyl group-containing NSAID.

To improve the cohesion of the pressure sensitive adhesive layer and, at the same time, the release of the active substance ibuprofen, the addition of an alkali hydroxide has been proposed in JP 4074119 A. The addition of a permeation-enhancing fatty acid is, however, not provided for in this document.

It was thus the object of the present invention to provide transdermal therapeutic systems which are suitable for administration of the above-mentioned active substances, and which stand out for their advantageous properties described in DE 198 30 649 A1, but do not have the above-described drawbacks.

Furthermore, it is demanded that it must be possible to prepare the NSAID-containing polymer matrix in non-aqueous medium, i.e. in organic solvents. This is of significance because the large majority of the carboxyl group-containing pressure-sensitive adhesives suitable for realizing the invention can be processed only in organic solution.

This object is achieved in a TTS having the features of the preamble of claim 1 by the fact that the active substance-containing matrix is prepared on the basis of a carboxyl group-containing polyacrylate pressure-sensitive adhesive, and that it has a content of oleic acid and of potassium ions, the constituent amount of the potassium ions being in the range of 5 to 50%, relative to the equivalent weight of the sum of all carboxyl group-containing matrix components.

It was found, surprisingly, that only by using oleic acid as permeation-enhancing fatty acid and potassium hydroxide as alkali hydroxide it is possible to prepare the active substance matrix in non-aqueous medium, typically in ethyl acetate. Precipitation of the fatty acid salt as insoluble precipitate does not occur in this case. The fact that no such precipitation occurs is presumably due to the specific properties of the oleic acid-potassium salt formed by the inventive addition of oleic acid and potassium ions. When other alkali fatty acid salts are used in the presence of an organic solvent, precipitation occurs (see examples 1 to 8, and Table 1).

Because of this advantageous property, resulting from the combination of oleic acid and potassium ions, it is in principle possible to use any carboxyl group-containing pressure-sensitive adhesives which are utilized in organic solution, e.g. the pressure-sensitive adhesives sold under the designation of "Durotak" by the firm of National Starch, to produce the matrix layers according to the invention.

Since in the TTS according to the invention, precipitation of oleic acid in the matrix can be reliably prevented, these TTS are characterized by a very homogeneous matrix layer; preferably, this matrix layer consists only of a single phase, i.e. it is not an emulsion or suspension or a multi-phase polymer mixture.

The matrix layers according to the present invention, compared to DE 198 30 649 A1, in addition possess a markedly improved cohesion of the pressure sensitive adhesive matrix layer and a perfect anchorage to backing layers of PET materials. Compared to JP 4074119, there results a substantial improvement in the skin permeation of the active substance due to the permeation-enhancing action of the oleic acid contained.

As carboxyl group-containing polyacrylate adhesives for the production of the active substance matrix according to the invention, the carboxyl group-containing pressure sensitive adhesives sold under the name of "Durotak" by the firm of National Starch are used with preference, especially the pressure sensitive adhesive Durotak 387-2353. Apart from these, other polyacrylate adhesives which are produced by free-radical polymerization of acrylic and/or methacrylic acid and their derivatives, e.g. 2-ethylhexyl acrylate, are in principle suitable as well. Additionally, such polymers may also contain further comonomers, e.g. vinyl acetate. In the individual case, suitable mixtures of different carboxyl group-containing polyacrylate pressure-sensitive adhesives may also be utilized.

The weight per unit area of the matrix layer is preferably in the range of from 30-120 g/m², a weight per unit area in the range of 50-80 g/m² being particularly preferred.

The potassium ions contained in the matrix layers of the present invention are preferably added as potassium hydroxide. Since the inventive formulations have at least three carboxyl group-containing components, namely the active substance, oleic acid, as well as the carboxyl group-containing pressure-sensitive adhesive, it can be determined only with great difficulty with which one of these carboxyl group-containing components salt formation occurs, and in what ratio. For this reason, an experimental study on this salt formation was dispensed with.

It is instead preferred to indicate the amount of the potassium hydroxide contained in percentage of the equivalent weight of the sum of the carboxyl group-containing components of the matrix (see Example 9). An amount of 100% of potassium hydroxide equivalents then corresponds to the neutralization of all carboxyl group-containing matrix components. It has been observed that a marked increase in the cohesion of the matrix film occurs only when at least an amount of 5%, better 10%, of potassium hydroxide equivalents is added. If, on the other hand, the added quantity of KOH exceeds a value of 50% of potassium hydroxide equivalents, the matrix layer or matrix film suffers a great loss in tackiness. At the same time, the hydrophilicity of the matrix strongly increases so that the matrix film blushes due to uptake of moisture when it is worn on the skin and its tackiness diminishes.

Preferably, KOH is added in an amount of from 10 to 40% of potassium hydroxide equivalents, with optimum results being achieved at ca. 30% of potassium hydroxide equivalents.

The content of oleic acid may amount to between 5 and 25%-wt., relative to the matrix layer; preferably, oleic acid is added in an amount of 10-20%-wt.

As active substances from the group of the carboxyl group-containing NSAID, preferably ibuprofen, flurbiprofen, fenoprofen, ketoprofen, naproxen, and tiaprofen are used, with ibuprofen being particularly preferred; other representatives of this group of active substances can, however, be used as well, for example the active substances mentioned at the beginning. With preference, the active substance is present substantially as (S)-enantiomer. The active substance concentration in the matrix preferably amounts to 5 to 25%-wt., with particular preference 10 to 20%-wt.

According to a special embodiment of the invention it is provided for the pressure sensitive adhesive to be present crosslinked by aluminum ions. As cross-linking reagent, preferably aluminum acetylacetonate is used. By crosslinking, the cohesion of the layer of adhesive is additionally improved. Aluminum acetylacetonate is preferably added in a concentration of from 0.01 to 0.2%-wt, the range of concentration of from 0.05 to 0.1%-wt being particularly preferred. The mentioned percentages are calculated as aluminum ion concentrations in the active substance-containing adhesive matrix.

Figure 2:
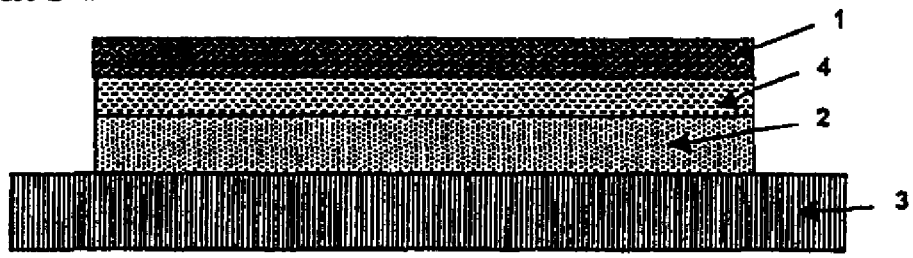

The present invention further comprises such embodiments wherein between the active substance-containing matrix layer of the TTS and its backing layer there is attached a water vapor-blocking intermediate layer which has an occlusive effect when the system is worn on the skin (see FIG. 2). This intermediate layer is preferably made up of hydrocarbon polymers, e.g. of polyisobutylene, polybutadiene, polyisoprene or block copolymers of the styrene with butadiene or isoprene. The weight per unit area of the intermediate layer lies in the range of from 10 to 100 g/m², preferably in the range of 20 to 80 m².

Providing such an intermediate layer is of advantage especially in those cases where the backing layer is made of water vapor-permeable material.

As the material for the backing layer of the inventive TTS, preferably polyethylene terephthalate (PET) film is used, with particular preference, however, lengthwise and crosswise elastic, air- and water vapor-permeable PET fabric. But other polyester films or fabrics known to those skilled in the art may be used as well, materials having elastic properties being preferred.

For the detachable protective layer plastic films are taken into consideration which have been rendered dehesive (e.g. through siliconization), for example plastic films of polyethylene, polyethylene terephthalate (PET) or of similar materials.

The structure of the TTS according to the invention will be explained by way of example with reference to FIGS. 1 and 2. These are schematic, simplified drawings each showing a TTS in sectional view.

FIG. 1 shows a TTS, consisting of a backing layer (1) and a homogeneous, active substance-containing matrix layer (2). The skin-facing side of the matrix layer (2) is covered by a detachable protective layer (3).

This preferred structure corresponds to the structure described in Example 9.

FIG. 2 shows a further preferred structure of a TTS according to the present invention, which structure likewise has a backing layer (1), a homogeneous, active substance-containing matrix layer (2) and a detachable protective layer (3). Additionally, between matrix layer (2) and backing layer (1) there is a water vapor-blocking intermediate layer (4).

EXAMPLES 1 TO 8

Solubility of Alkali Fatty Acid Salts

The tests were performed as follows: The fatty acid indicated in Table 1 was dissolved in ethyl acetate at a concentration of 10%-wt. Subsequently, 2 drops of a solution of the indicated alkali hydroxide in methanol (10%-wt) were added to the solution. It was recorded if a white precipitate (N) occurred at the dropping site, or if the solution remained clear (K). The results are shown in Table 1.

TABLE 1

|   | Lauric acid | | Myristic acid | | Stearic acid | | Oleic acid | |
| --- | --- | --- | --- | --- | --- | --- | --- | --- |
| NaOH | Expl. 1 | N | Expl. 2 | N | Expl. 3 | N | Expl. 4 | N |
| KOH | Expl. 5 | N | Expl. 6 | N | Expl. 7 | N | Expl. 8 | K |

Among the fatty acids most frequently used in the production of TTS, only the potassium salt of the oleic acid proved to be soluble in ethyl acetate (Example 8).

EXAMPLE 9

Preparation of a TTS Containing The Active Substance Ibuprofen

Composition:

|  | % wt. | Equivalent weight of KOH (in mg KOH/g substance) |
|---|---|---|
| Ibuprofen | 16.63 | 270 |
| Oleic acid | 16.63 | 199 |
| Potassium hydroxide | 3.16** | — |
| Aluminium* | 0.1 | — |
| Durotak 387-2353 | 63.48 | 49 |
| Sum: | 100.00 | |

The percentages relate to the matrix weight.
*crosslinkingly bound to the pressure-sensitive adhesive polymer
**this portion corresponds to 29% of the equivalent weight of the sum of all carboxyl group-containing components.

Preparation

To prepare Example 9, first, oleic acid is stirred into the Durotak pressure-sensitive adhesive solution (Durotak 387-2353; the firm of National Starch). Thereafter, potassium hydroxide in the form of a 10% (%-wt.) solution in methanol is slowly added while stirring. Finally, ibuprofen is dissolved in this preparation, and the pulverulent cross-linking reagent aluminum acetylacetonate is added and stirred in until dissolution. To adjust a viscosity suitable for the coating, ethyl acetate is added to the finished solution according to requirements.

This adhesive solution is coated to a siliconized polyester film (PET, 100 μm). The coating thickness is adjusted such that after 10 minutes of drying at 60° C. in a drawing-off air oven a film having a weight per unit area of from 60 to 80 g/m$^2$ is obtained. The dried film of adhesive is provided with a lengthwise and crosswise elastic PET fabric (by the firm of KOB Karl Otto Braun) as backing layer. Subsequently, individual patches of suitable size and shape are punched out of this laminate.

The invention claimed is:

1. Transdermal therapeutic system (TTS) with a content of at least one active substance from the group of the carboxyl group-containing non-steroidal antirheumatics, which has a backing layer (1), an active substance-containing matrix layer (2) and a detachable protective layer (3), wherein a matrix layer (2) is based on a carboxyl group-containing polyacrylate pressure-sensitive adhesive, which matrix layer (2) has a content of oleic acid and potassium ions, with the constituent amount of the potassium ions being in the range of from 5 to 50%, relative to the equivalent weight of the sum of all carboxyl group-containing matrix components.

2. The TTS according to claim 1, wherein the constituent amount of the potassium ions is in the range of from 10 to 40%, relative to the equivalent weight of the sum of all carboxyl group-containing matrix components.

3. The TTS according to claim 1 or 2, wherein the content of oleic acid in the matrix layer is 5 to 25%-wt.

4. The TTS according to claim 1, wherein the active substance is present as the (S)-enantiomer.

5. The TTS according to claim 1, wherein the active substance concentration in the active substance-containing matrix amounts to 5 to 25%-wt.

6. The TTS according to claim 1, wherein the carboxyl group-containing pressure-sensitive adhesive polymer matrix is cross-linked by aluminum ions.

7. The TTS according to claim 1, wherein the matrix layer is of a homogeneous structure and consists of a single phase only.

8. The TTS according to claim 1, wherein the backing layer consists of polyester film.

9. The TTS according to claim 1, wherein between the active substance-containing matrix layer and the backing layer there is arranged a water vapor-blocking intermediate layer which is made up of hydrocarbon polymers, with the weight per unit area of the intermediate layer being 10 to 100 g/m$^2$.

10. A process for the production of a transdermal therapeutic system (TTS) having a content of at least one active substance from the group of the carboxyl group-containing non-steroidal antirheumatics, which system has a backing layer, an active substance-containing matrix layer based on a carboxyl group-containing polyacrylate pressure sensitive adhesive, and a detachable protective layer, comprising the following steps:

a) providing the carboxyl group-containing polyacrylate pressure-sensitive adhesive in organic solution;

b) adding 5 to 25%-wt. of oleic acid, by stirring;

c) adding KOH in 10% solution (%-wt.) of methanolic solution under stirring, with the amount of KOH being in the range of from 5 to 50%, relative to the equivalent weight of the sum of all carboxyl group-containing matrix components;

d) adding the active substance from the group of the carboxyl group-containing non-steroidal antirheumatics, which active substance is dissolved in the pressure-sensitive adhesive preparation by stirring;

e) adding aluminum acetylacetonate in pulverulent form and stirring until complete solution occurs, with the concentration of the aluminum acetylacetonate being 0.01 to 0.2%-wt calculated as aluminum ions in the active substance-containing adhesive matrix;

f) coating the pressure-sensitive adhesive solution to a siliconized polyester film, and drying in order to remove the solvents;

g) covering the dried layer with an elastic polyester film or an elastic polyester fabric as backing layer; and h) punching out individual TTS.

11. The process according to claim 10, comprising the following step f), wherein the dried layer of pressure-sensitive adhesive is covered with an intermediate layer of hydrocarbon polymers to which subsequently the backing layer is applied (step g), with the hydrocarbon polymers being selected from the group of polyisobutylene, polybutadiene, polyisoprene or block copolymers of styrene with butadiene or isoprene.

12. The TTS according to claim 3, wherein the content of oleic acid in the matrix layer is 10 to 20%-wt.

13. The TTS according to claim 5, wherein the active substance concentration in the active substance-containing matrix amounts to 10 to 20%-wt.

14. The TTS according to claim 8, wherein the polyester film is selected from the group consisting of polyethylene terephthalate films and elastic polyester fabric.

15. Process according to claim 10 for the production of a transdermal therapeutic system (TTS); wherein the concentration of the aluminum acetylacetonate is 0.05 to 0.1%-wt calculated as aluminum ions in the active substance-containing adhesive matrix.

16. The TTS according to claim 1, wherein it contains at least one active substance selected from the group consisting of propionic acid derivatives and acetic acid derivatives of non-steroidal antiphlogistics.

17. The TTS according to claim 16, wherein the at least one active substance is selected from the group consisting essentially of indomethacin, acemetacin, tolmetin, diclofenac, lonazolac, ibuprofen, flurbiprofen, fenoprofen, ketoprofen, naproxen, and tiaprofen.

18. The TTS according to claim 1, wherein between the active substance-containing matrix layer and the backing layer there is arranged a water vapor-blocking intermediate layer which is preferably made up of hydrocarbon polymers, with the weight per unit area of the intermediate layer being 20 to 80 $g/m^2$.

* * * * *